United States Patent [19]

Moulding, Jr.

[11] Patent Number: 4,601,698

[45] Date of Patent: Jul. 22, 1986

[54] METHOD OF AND INSTRUMENT FOR INJECTING A FLUID INTO A UTERINE CAVITY AND FOR DISPERSING THE FLUID INTO THE FALLOPIAN TUBES

[76] Inventor: Thomas S. Moulding, Jr., 109 Via El Chico, Redondo Beach, Calif. 90277

[21] Appl. No.: 651,297

[22] Filed: Sep. 17, 1984

[51] Int. Cl.⁴ .............................................. A61B 19/00
[52] U.S. Cl. ........................................ 604/55; 604/22; 128/1 R
[58] Field of Search ........................................ 128/1 R

[56] References Cited

U.S. PATENT DOCUMENTS

| | | | |
|---|---|---|---|
| 3,805,767 | 4/1974 | Erb | 128/1 R |
| 3,871,374 | 3/1975 | Bolduc | 128/1 R |
| 3,918,431 | 11/1975 | Sinnreich | 128/1 R |
| 3,948,259 | 4/1976 | Bolduc | 128/1 R |

Primary Examiner—Peter D. Rosenberg

[57] ABSTRACT

A method of female sterilization comprising the steps of providing a toxic fluid capable of damaging the fallopian tubes which leads to their ultimate occlusion, injecting the fluid into the uterine cavity of the female, and vibrating the fluid within the uterine cavity. Preferably, the fluid is vibrated at ultrasonic frequencies for a time period in the time range of between five seconds and ten minutes. The device used to inject the fluid into the uterine cavity may be used to produce the vibration, and the vibration may be directed at the uterus, which in turn indirectly causes the fluid in the cavity to vibrate. An instrument for performing the method is also disclosed.

16 Claims, 3 Drawing Figures

METHOD OF AND INSTRUMENT FOR INJECTING A FLUID INTO A UTERINE CAVITY AND FOR DISPERSING THE FLUID INTO THE FALLOPIAN TUBES

BACKGROUND OF THE INVENTION

The population explosion problem is particularly acute in many underdeveloped countries of the world. The governments of many of these countries seek to solve the population explosion problem by offering voluntary sterilization services to its adult citizens through various government sponsored incentives and programs. Surgical methods of sterilization have proved to be unsatisfactory primarily for four reasons: surgical techniques are relatively expensive; surgery often forces the patient to stay away from home at a hospital or health care facility; surgery can be painful when performed on an out patient basis; and rare, adverse reactions to surgery cause the citizens to become superstitious and fearful of surgery. Consequently, efforts have intensified over the last twenty years to use transcervical techniques to achieve sterilization by occlusion of the oviducts. Although transcervical techniques have been used for at least one hundred years, they still do not achieve sterilization in a relatively large percent of women.

The use of various toxic chemicals such as quinacrine, to achieve oviduct occlusion has been reviewed in a recent article by R. M. Richard in "Research Frontiers In Fertility Regulation", Vol. I, No. 5 (December 1981) and in a book entitled "Female Transcervical Sterilization" edited by Zatuchni, Shelton, Goldsmith, and Sciarra and published by Harper & Row. All of the methods described are based on the principle that the fluid damages the oviducts and the subsequent healing processes occlude the oviducts. Experiments performed by the inventor and others indicate that non-penetration of the toxic fluid into the oviducts is at least one of the reasons that chemicals such as quinacrine fail to occlude the oviducts in a large number of cases. Also, further experiments performed by the inventor and others indicate that such non-penetration is attributable to adhesive forces that hold the oviduct folds together or to spasm of the muscles of the uterus surrounding the oviducts. A relatively high rate of oviduct occlusion has been achieved by multiple injections of a toxic fluid into the uterine cavity and by injecting the toxic fluids into the intrauterine cavity under pressure. The procedure of multiple injections suffers from the drawback that the patient must visit a doctor or clinic on several occasions. The procedure of pressurizing the toxic fluid suffers from two major drawbacks. First, this procedure uses excessive amounts of the toxic fluid, which sometimes causes the fluid to flow through one or both fallopian tubes into the peritoneal cavity, which in turn can damage the peritoneal cavity or cause the toxic fluid to be injected into the blood stream. Second, this procedure sometimes causes one fallopian tube to open before the other fallopian tube, thereby reducing the intrauterine pressure and making it difficult for the other fallopian tube to open.

The present invention was developed primarily in an effort to find a quick, inexpensive, safe and highly successful transcervical technique of oviduct occlusion by injecting toxic fluids into the intrauterine cavity and the fallopian tubes.

SUMMARY OF THE INVENTION

The present invention relates to a method of female sterilization comprising the steps of providing a toxic fluid capable of occluding the fallopian tubes, injecting the fluid into the uterine cavity of the female, and vibrating the fluid within the uterine cavity. Preferably, the fluid is vibrated for a time period in the time range of between five minutes and ten minutes. The device used to inject the fluid into the uterine cavity may be used to produce the vibration, and the vibration may be directed at the uterus, which in turn indirectly causes the fluid in the cavity and the fallopian tubes to vibrate. An instrument for performing the method is also disclosed.

BRIEF DESCRIPTION OF THE DRAWINGS

The invention will be described with reference to the accompanying drawings, wherein.

DESCRIPTION OF A PREFERRED EMBODIMENT

Figure 1:
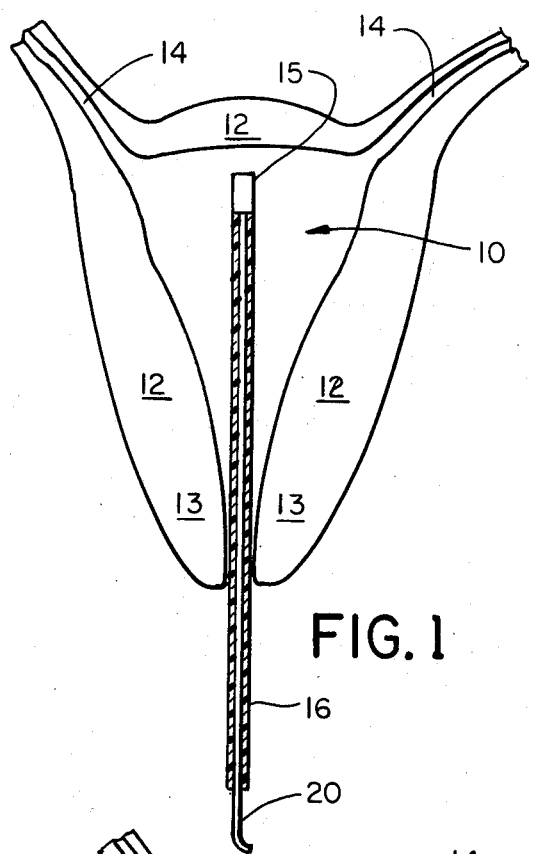
FIG. 1 is a schematic, front view of the uterine cavity and an instrument that may be used to perform the method in accordance with one embodiment of the present invention.
Figure 2:
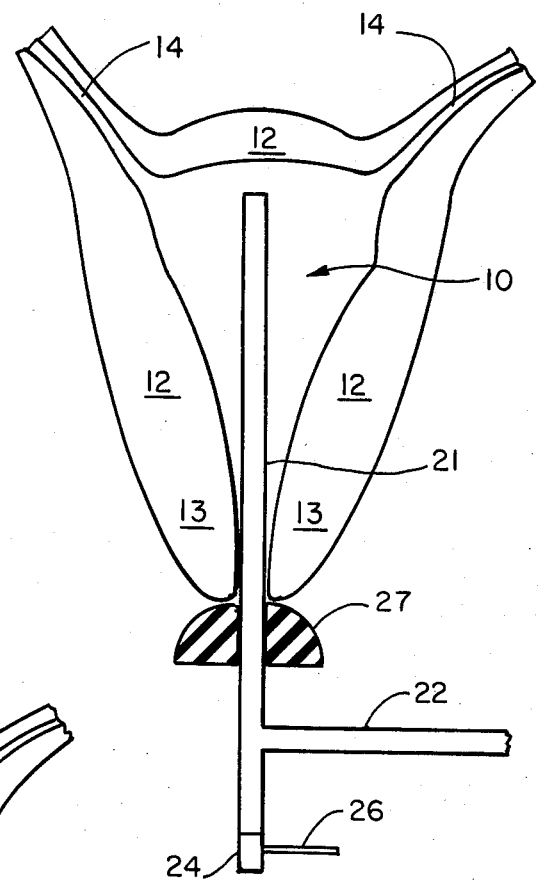
FIG. 2 is a schematic, front view of the intrauterine cavity and an instrument in accordance with another embodiment of the present invention.
Figure 3:
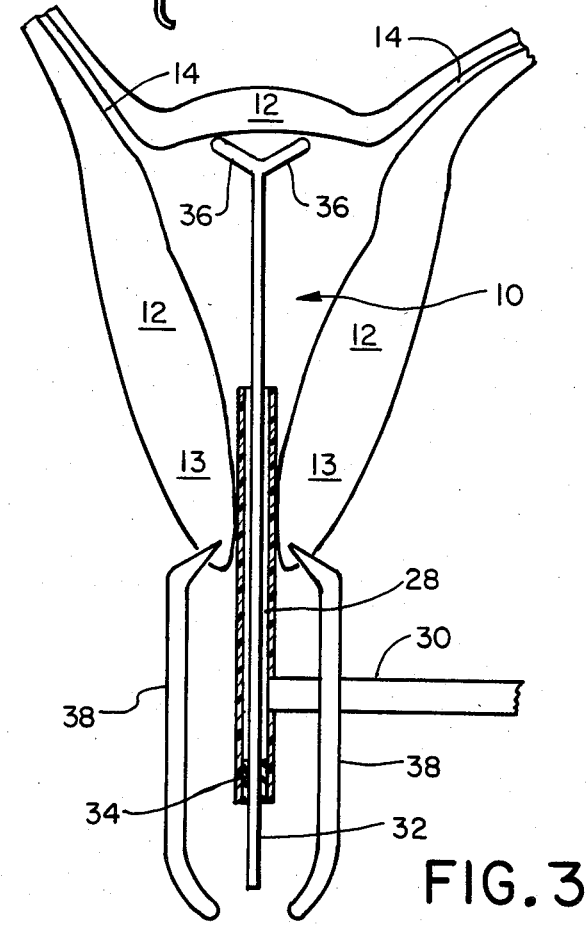
FIG. 3 is a schematic, front view of the uterine cavity and an instrument in accordance with yet another embodiment of the present invention.

Referring now to the drawings wherein like reference numerals and symbols refer to the same item, there is shown in FIGS. 1 through 3 a uterine cavity 10 formed by the uterus 12 and the cervix 13. A pair of oviducts or fallopian tubes 14 communicate with the uterine cavity 10.

In accordance with the embodiment of the invention depicted in FIG. 1, a fluid capable of occluding the fallopian tubes 14, such as a suspension of quinacrine in water, is injected by any of a variety of well known means into the uterine cavity 10. A cannula 16 is then partially inserted into the uterine cavity 10. The end of the cannula 16 adapted for extension into the uterine cavity 10 is provided with a vibrating device such as a piezo electric crystal 18 which serves to cap the cannula end. A wire 20 extends through the cannula 16 and operatively connects the piezo electric crystal 18 with an electric energy source (not shown). The piezo electric crystal 18 is selectively vibrated preferably for a time period in the range of between five minutes and ten minutes such that the fluid injected into the uterine cavity vibrates in response to the piezo electric crystal 18, whereby the penetration of the fluid into the fallopian tubes 14 is promoted. It should be apparent that vibrating mechanisms other than a piezo electric crystal, such as an electromagnetic linear activator, can be used in accordance with the embodiment of the invention shown in FIG. 1.

It should also be apparent that many types of devices other than the instrument shown in FIG. 1 can be used to vibrate the fluid within the uterine cavity 10. Such devices might include a rod which is vibrated either longitudinally, laterally, or rotationally.

There is shown in FIG. 2 yet another instrument constructed according to another embodiment of the present invention. A cannula 21 is provided for at least partial insertion into the uterine cavity 10. The cannula 21 can be surrounded by an acorn shaped object 27 preferably fashioned of rubber, which can be used to occlude the cervix 13, thereby inhibiting the leakage of fluids from the uterine cavity 10 through the cervix 13 and into the vagina. This can be accomplished by advancing the cannula 21 until the acorn shaped object 27 mounted around the cannula 21 abuts the cervix 13. The interior of the cannula 21 communicates with a tube 22 to a source of a fluid (not shown) capable of damaging the fallopian tubes 14 and ultimately causing their occlusion. The end of the cannula 21 adapted to be disposed outside the uterine cavity 10 is capped with a vibrating device such as a piezo electric crystal 24 connected through a wire 26 to an electrical energy source (not shown). Again, vibrating mechanisms other than the piezo electric crystal 24 can be utilized, such as an electromagnetic linear activator, a fluidic oscillator, a diaphragm, etc.

Another instrument that may be used in place of the instrument shown in FIG. 1 is the so-called Femcept device described in U.S. Pat. No. 4,207,891 to Bulduc and in other related, earlier patents by the same inventor. The Femcept device includes an expandable balloon surrounded in its lower portion by a mesh of string adapted for inserting toxic fluid chemicals into the uterine cavity. To achieve vibration of the fluid introduced by the Femcept device, either the liquid in the channel of the Femcept device leading to the uterine cornua could be vibrated or the gas within the channel which leads to the intrauterine balloon of the Femcept device could be vibrated. Also, the entire Femcept device could be vibrated. In this application of the invention, the duration of vibration would preferably be for a time period in the range of ten to one hundred seconds.

The uterus, and in turn any fluid within the uterine cavity, may be vibrated by vibrating a tenaculum attached to the cervix or by vibrating a suction cup attached to the cervix in a usual manner. Many other instruments adapted for extension into the uterine cavity can also be vibrated for advantageous use in the present invention.

Still another instrument in accordance with yet another embodiment of the present invention is depicted in FIG. 3. The instrument includes a cannula 28 adapted to at least partially extend into the uterine cavity 10. The cannula 28 can be surrounded by an acorn shaped object identical to that shown in FIG. 2. The interior of the cannula 28 communicates through a tube 30 to a source of fluid (not shown) capable of entering, damaging, and ultimately occluding the fallopian tubes 14. A uterine sound 32 extends through and is translatable within the cannula 28. A packing material such as a TEFLON coated washer 34 surrounds the uterine sound 32 within the end of the cannula 28 adapted to be disposed outside the uterine cavity 10. The TEFLON coated washer 34 prevents fluid flowing from the tube 30 into the cannula 28 from flowing out of the cannula 28 other than from the end of the cannula 28 extending into the uterine cavity 10. The end of the uterine sound 32 adapted to extend into the uterine cavity 10 is provided with a plurality of branch sounds 36 (two of which are shown in FIG. 3). The branch sounds 36 are adapted to contact the uterus 12. The uterine sound 32 may be vibrated by any one of a variety of well known means either longitudinally or rotationally. Such vibration of the uterine sound 32, and concomitantly the branch sounds 36, causes the fluid within the uterine cavity 10 to be vibrated. Moreover, the contact between the branch sounds 36 and the uterus 12 causes the uterus and tissues surrounding the uterus to vibrate, which promotes the flow of fluid into the fallopian tubes 14. The sound 32 with branch sounds 36 can be used together with a tenaculum 38 attached to the cervix 13 as shown in FIG. 3. The vibrations of the sound 32 with branch sounds 36 can be coordinated with the vibrations of the tenaculum 38 by any of a variety of vibrating means such that the two instruments move in opposite directions. Such opposing vibratory movement alternately stretches and relaxes the tissues surrounding the intrauterine portion of the fallopian tubes to promote the flow of fluid into the fallopian tubes. Specifically, when the branch sounds 36 move relatively away from the tenaculum 38, they will stretch the tissues surrounding the fallopian tubes and when the branch sounds 36 move relatively toward the tenaculum 38, they will relax the tissues. It should be appreciated that the instruments depicted in both FIGS. 2 and 3 can cause the vibration to occur either as the fluid is injected into the uterine cavity, after the fluid is injected into the uterine cavity, or both.

Although particular embodiments of the present invention have been described and illustrated herein, it should be recognized that modifications and variations may readily occur to those skilled in the art and that such modifications and variations may be made without departing from the spirit and the scope of my invention. Consequently, my invention as claimed below may be practiced otherwise than is specifically described above.

I claim:

1. An instrument for injecting a fluid into a uterine cavity and for dispersing the fluid into the fallopian tubes comprising:
   a tube having an open end adapted for insertion into the uterine cavity, the interior of said tube adapted for communication with a source of fluid whereby fluid from the source of fluid may flow through said tube and into the uterine cavity; and
   means for vibrating the fluid within the uterine cavity whereby the fluid is dispersed into the fallopian tubes.

2. An instrument according to claim 1 wherein said vibrating means is mounted on said tube.

3. An instrument according to claim 1 wherein said vibrating means is capable of vibrating at ultra sonic frequencies.

4. An instrument according to claim 1 further comprising a rod extending through the interior of said tube and adapted to extend beyond the open end of said tube and wherein said vibrating means vibrates said rod.

5. An instrument according to claim 4 wherein said rod comprises a uterine sound having a plurality of branch sounds in the region of said uterine sound that is adapted to extend beyond the open end of said tube.

6. A method of dispersing a fluid into fallopian tubes comprising the steps of:
   injecting the fluid into the uterine cavity; and
   vibrating the fluid within the uterine cavity.

7. A method of dispersing a fluid into the fallopian tubes according to claim 6 wherein said vibrating is at ultra sound frequencies.

8. A method of dispersing a fluid into fallopian tubes according to claim 6 wherein said vibrating occurs for a duration in the range of between five seconds and ten minutes.

9. A method of dispersing a fluid into fallopian tubes according to claim 6 comprising the step of vibrating the uterus, which in turn causes the fluid within the uterine cavity to vibrate.

10. A method of dispersing a fluid into fallopian tubes according to claim 6 wherein said fluid includes a chemical capable of occluding the fallopian tubes.

11. A method of female sterilization comprising the steps of:
providing a fluid capable of damaging the fallopian tubes of a female upon contact between the fluid and the fallopian tubes;
injecting the fluid into the uterine cavity of the female; and
vibrating the fluid within the uterine cavity.

12. A method of dispersing a fluid into a tubular structure in the tissue of a living animal, the interior of which tubular structure is in communication with a cavity also formed and defined by the tissue of said living animal, comprising the steps of:
injecting the fluid into said cavity; and
vibrating the fluid within said cavity.

13. A method of dispersing a fluid into a tubular structure according to claim 12 wherein said vibrating is at ultra sound frequencies.

14. A method of dispersing a fluid into a tubular structure according to claim 12 wherein said vibrating means occurs for a duration in the range of between five minutes and ten minutes.

15. A method of dispersing a fluid into a tubular structure according to claim 12 comprising the step of vibrating the tissues surrounding said tubular structure, which in turn causes the fluid within said structure to vibrate.

16. A method of dispersing a fluid into a tubular structure according to claim 12 wherein said fluid includes a chemical capable of occluding the tubular structure.

* * * * *